(12) United States Patent
Park et al.

(10) Patent No.: US 7,294,467 B2
(45) Date of Patent: Nov. 13, 2007

(54) QUANTITATIVE ANALYSIS OF DNA

(75) Inventors: Sang-Ryoul Park, Daejeon (KR);
In-Chul Yang, Daejeon (KR);
Myung-Sub Han, Daejeon (KR);
Yong-Hyeon Yim, Daejeon (KR);
Eui-Jin Hwang, Daejeon (KR)

(73) Assignee: Korea Research Institute of Standard and Science (KR)

( * ) Notice: Subject to any disclaimer, the term of this patent is extended or adjusted under 35 U.S.C. 154(b) by 243 days.

(21) Appl. No.: 11/138,981

(22) Filed: May 26, 2005

(65) Prior Publication Data

US 2006/0078905 A1    Apr. 13, 2006

(30) Foreign Application Priority Data

Oct. 13, 2004    (KR) .................... 10-2004-0081611

(51) Int. Cl.
*C12Q 1/68* (2006.01)
*C07H 1/00* (2006.01)
*C07H 19/00* (2006.01)
*C07H 21/00* (2006.01)

(52) U.S. Cl. .................... 435/6; 536/22.1; 536/124

(58) Field of Classification Search .................... 435/6; 536/22.1, 124
See application file for complete search history.

(56) References Cited

OTHER PUBLICATIONS

Baginski et al., Microdetermination of nucleiic acid phosphate. Microchemical J. 13 : 115-119 (1968).*
Kirkpatrick et al., Simplified wet ash procedure for total phosphorus analysis of organophosphates in biological samples. Analytical Chemistry 43(12) :1707-1709 (1971).*
Fiske et al, The colorimetric determination of phosphorus. J. of Biological Chemistry 66:375-400(1925).*
Chen et al., Microdetermination of phosphorus 28: 1756-1758 (1956).*
"MALDI on a Chip: Analysis of Arrays of Low-Femtomole to Subfemtomole Quantities of Synthetic Olignucleotides and DNA Diagnostic Products Dispensed by a Piezoeletric Pipet"; Authors: Daniel P. Little, et al.; Anal. Chem., vol. 69, No. 22; Nov. 15, 1997; pp. 4540-4546.
"Matrix-Assisted Laser Desorption/Ionization Mass Spectrometry Methods for Oligodeoxynucleotides: Improvements in Matrix, Detection Limits, Quantification, and Sequencing"; Authors: Li-Kang Zhang and Michael L. Gross; American Society for Mass Spectrometry; 2000; pp. 854-865.
"Quantitation of Oligonucleotides by Phosphodiestrerase Digestion Followed by Isotope Dilution Mass Spectrometry: Proof of Concept"; Authors: Gavin O'Connor, et al.; Anal. Chem., vol. 74, No. 15; Aug. 1, 2002; pp. 3670-3676.
"Revised UV extinction coefficients for necleoside-5'-monophosphates and unpaired DNA and RNA"; Authors: Michael J. Cavaluzzi and Philip N. Borer; Nucleic Acids Research, vol. 32, No. 1; 2004; pp. 1-9.
"A Comparison of Measured and Calculated Single- and Double-Stranded Oligodeoxynucleotide Extinction Coefficients"; Authors: Gary Kallansrud and Brian Ward; Analytical Biochemistry, vol. 236, Article No. 0141; 1996; pp. 134-138.
Techanical Brief—"Quantifying DNA concentrations using fluorometry: A comparison of fluorophores"; Authors: Kalpana Rengarajan, et al.; Molecular Vision, vol. 8; 2002; pp. 416-421.
"Characteristics of Different Nucleic Acid Staining Dyes for DNA Fragment Sizing by Flow Cytometry"; Authors: Xiamei Yan, et al.; Anal. Chem., vol. 71, 1999, pp. 5470-5480.
"Concentration and Extinction Coefficient Determination for Oligonucleotides and Analogs Using a General Phosphate Analysis"; Authors: James H. Murphy and Tina L. Trapane; Analytical Biochemistry, vol. 240, Article No. 0357; 1996; pp. 273-282.

* cited by examiner

*Primary Examiner*—Ethan Whisenant
(74) *Attorney, Agent, or Firm*—Cantor Colburn LLP

(57) ABSTRACT

The present invention is related to a novel approach for quantitation of DNA based on the stoichiometric existence of phosphorus (P) in DNA.

5 Claims, 3 Drawing Sheets

SEQUENCE LISTING

<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: synthsized
<220> FEATURE:
<221> NAME/KEY: modified_base
<222> LOCATION: (1)..(1)
<223> OTHER INFORMATION: n is hydroxlyated thymine
<220> FEATURE:
<221> NAME/KEY: modified_base
<222> LOCATION: (20)..(20)
<223> OTHER INFORMATION: n is hydroxlyated guanine

<400> SEQUENCE: 1
naatacgact cactataggn                    20

<210> SEQ ID NO 2
<211> LENGTH: 19
<212> TYPE: DNA
<213> ORGANISM: Artificial
<220> FEATURE:
<223> OTHER INFORMATION: synthsized

<400> SEQUENCE: 2

-continued

```
aatacgactc actataggg                                    19

<210> SEQ ID NO 3
<211> LENGTH: 18
<212> TYPE: DNA
<213> ORGANISM: Artificial
<220> FEATURE:
<223> OTHER INFORMATION: synthsized

<400> SEQUENCE: 3
atacgactca ctataggg                                     18
```

QUANTITATIVE ANALYSIS OF DNA

TECHNICAL FIELD

The present invention is related to a method of quantitative analysis of DNA based on the stoichiometric existence of phosphorus (P) in DNA, in which the quantity of DNA oligomers may be measured more accurately by removing uncertainties in quantitation.

PRIOR ART

DNA oligomers are materials that are chemically synthesized by professional manufacturing companies as designed by consumers, and their lengths reach 10 to 60 base units usually. Such synthetic DNA oligomers are not only used in a large quantity as primers, that are one kind of core reaction original materials of polymerase chain reaction (PCR), which is the nucleus of modern biotechnology but also used frequently as probes for detection or capture of specific nucleic acids various bioassay technologies. Also, to be noted are that they are utilized greatly as industrially valuable antisense drugs, and they are used as the agents for RNA interference spotlighted recently.

Because of such utilities, the accuracy of quantitation may be an important concern. Particularly, in the field of DNA chip technology, since the accuracy of the quantity of DNA oligomers used determines the accuracy of the chip technology eventually, and the accuracy of quantitative analysis of DNA has a significant meaning as a measure for determining the confidence of many results of related experiments and intercomparability among laboratories, an accurate quantitation of oligomers is of great interest.

The analytical technique attracting attention in connection with the analysis of DNA is mass spectrometry. (Little, D. P. et al., Anal. Chem., 69, 1997, 4540-4546.; Zhang L. K. et al., J. Am. Soc. Mass. Spectrom., 11, 2000, 854-865). Although it is expected that mass spectroscopy is positioned to be an accurate quantitative analysis in the field of biology, it is limited technically in the accurate quantitation of polymeric molecules such as DNA, proteins, etc. In the field of qualitative analysis, the structures of polymeric molecules may be investigated accurately by utilizing high resolution mass spectroscopy such as ICR-FTMS. However, in a quantitative aspect, mass spectroscopy fails to provide with satisfactory results yet. That is, if the size of molecules is large during ionization wherein samples are introduced into a mass spectroscope, the accuracy of mass spectroscopy of polymeric molecules remains around 10% since a complex ionization phenomenon occurs and such phenomenon is not likely to recur. This uncertainty is too large in order for mass spectroscopy to be used for establishing standards for measurement. In order to overcome such problem with mass spectroscopy, O'Conner and others have attempted a method of cutting DNA into oligonucleotide units by using enzymes and analyzing them quantitatively with isotopic dilution HPLC-MS. (O'Connor, G. et al., Anal. Chem., 74, 2002, 3670-3676.)

The analytical techniques used frequently for the quantitation of DNA have been the measurement of UV absorbance and fluorescence using DNA intercalator. However, in case of UV absorbance, the quantity of DNA is only a crude approximation. Since bases bringing about light absorption actually have very different degrees of light absorption according to their types, the estimation of concentration without taking into consideration of base sequence may bring about great uncertainties. For this reason, there is a method of summing up the extinction coefficients of bases and the numbers of bases in the corresponding DNA. However, this method results in overestimation of extinction coefficients usually, which amounts to as high as 24%. (Cavaluzzi, M. J. et al., 2004, Nucleic Acids Res., 32, e13, 19.) It is because the hypochromicity effects caused by stacking among bases is ignored.

A "nearest-neighbor estimates" method with the interaction among neighboring bases taken into consideration is proposed and applied in order to reduce such uncertainties. (Kallansrud, G. et al., Anal. Biochem., 236, 1996, 134-138.) It has been reported from the results of a part of experiments that, in most cases, such consideration has improved the estimation of concentration, but absorption coefficients have been overestimated by about 14% in spite of such consideration. Therefore, the method of calculation of the concentration of DNA based on UV absorbance is not deemed to be a definitive method of quantitation.

A method of determining the concentration of DNA by measuring the fluorescence from dyes intercalated into DNA has been known to be a very sensitive method of analysis. Since the number of dye molecules intercalated into DNA is proportional to the number of bases of DNA, a linear relationship is established between the fluorescence measured and the concentration of DNA. (Rengarajan, K. et al., Mol. Vis., 8, 2003, 416-421.; Yan, X. et al., Anal. Chem., 71, 1999, 5470-5480.) It is, therefore, possible to calculate the concentration of DNA by measuring fluorescence. However, since the strength of fluorescence is affected by not only the quantity of DNA simply but also many other parameters such as dye concentration, degree of bleaching, intensity of excitation light, optics, geometry of a measurement cell, etc., it is difficult to guarantee the accuracy of measurement unless accurate standards for measurement are used.

The current shortfall in the comparability of quantitation of DNA can be improved substantially by providing high-quality measurement standards. For this, the producers of DNA reference materials need to establish a metrologically sound analytical method that has an inherent capability of absolute quantitation of DNA authentically. One immediate idea for this is to reduce complicated polymetric DNA materials down to smaller chemical species that make highly accurate quantitation feasible. From this point of view, O'Connor et al.'s approach is outstanding. (O'Connor, G et al., Anal. Chem., 74, 2002, 3670-3676.) They separated DNA oligomers into individual units by using enzymes, quantitated them by using HPLC-MS, and calculated backward the amount of DNA again. The results were highly reproducible, and the total spread of the results was less than 2%. However, in order to realize the advantage of this approach completely, the purity of nucleosides, that are base materials, first should be evaluated with high accuracy. Also, the digestion efficiency of phosphodiesterase, which is an enzyme used for digestion, should be ensured strictly.

It has been reported by Cavaluzzi and Borer that DNA oligomers might have been quantitated accurately by using NMR spectroscopy. (Nucleic Acids Res., 32, 2004, e13, 19.) A 18-mer oligomer was digested by using an enzyme, and individual nucleoside was analyzed by NMR spectroscopy. The accuracy of the procedure was estimated to be within 2-5%. The researchers used the analytical procedure for the evaluation of the accuracy of UV OD-based determination of the concentrations of oligomers. They also applied Murphy and Trapane's method. (Murphy, J. H. and Trapane, T. L., Anal. Biochem., 240, 1996, 273-283.) Murphy and Trapane digested oligomers to convert the phosphorus (P) in their phosphodiester bonds into phosphate ions. Then they determined phosphate concentration by using phosphomolybdate colorimetric assay. It has been reported that the relative standard deviation of this method has been less than 4%. Because DNA materials have one phosphodiester bond per base unit, the number of moles of a DNA molecule may be confidently calculated from the number of moles of phosphate from the DNA as long as the number of bonds in DNA molecules is known.

SUMMARY OF THE INVENTION

As reviewed in the above, the present invention is provide with a new quantitation technique of DNA oligomers, in which the quantity of DNA oligomers may be measured more accurately by removing uncertainties in quantitation further.

It is, therefore, an object of the present invention to provide with a method of quantitative analysis of DNA based on the stoichiometric existence of phosphorus (P) in DNA in order to develop quantitation techniques of DNA.

It is another object of the present invention to provide with a method of quantitation of plasmid DNA, genomes, and RNA.

In the present invention, DNA is put into closed vessels, and decomposed completely through microwave-aided acid digestion. Then, phosphorus is digested into inorganic phosphorus completely, and the resulting inorganic phosphorus is analyzed by using inductively coupled plasma-optical emission spectrometry (ICP-OES). The number of moles of phosphorus is obtained, and further from this, the number of moles of DNA is obtained stoichiometrically.

More concretely, the present invention is related to a method of quantitation of DNA oligomers, plasmid DNA, genomes, or RNA comprising the steps of:

1) melting a nucleotide with deionized water, and cleaning up by filtering by means of utrafiltration and other methods;

2) cleaning up the nucleotide by repeating the above step 1) more than two times;

3) acid digestion of the nucleotide at a high temperature by adding distilled hydrochloric acid into the analytical samples in the above step 2); and 4) analyzing the acid-digested samples by using ICP-OES.

The present invention is illustrated in more detail as follows:

The above step of cleanup in the present invention may be performed in various ranges within the confidence interval. It is preferable to melt a freeze-dried oligomer and clean up with Centricon YM-3 columns (Millipore, Bedford, Mass., USA). The primary cleanup is done by melting 70 to 80 mg of thus manufactured oligomer in 120 mL of deionized water, adding about 2 mL each of the solution into each column, and filtering by centrifugation, where it is preferable to adjust the temperature of the chamber to 8 to 12° C. and to centrifuge for about 2 hours with a centrifugal force of about 7000×g. For further cleanup, columns are washed with 2 mL of deionized water by centrifugation for about 2 hours at a centrifugal force of 7000 g. The washing process is repeated two or more times, after which each column retentate is recovered in approximately 1 mL of deionized water and pooled.

In the step of acid digestion, DNA is converted into an inorganic substance completely in the microwave-aided acid digestion method by putting DNA into closed vessels and adding hydrochloric acid distilled at a low temperature.

In the step of cleanup, these resulting materials are analyzed accurately in the ICP-OES analytical method in order to obtain the number of moles of phosphorus, and further, the number of moles of DNA based on the stoichiometric existence of phosphorus in DNA.

The present invention can further provide with a method of quantitation of plasmid DNA and/or genomic DNA, or RNA in addition to oligomers by using the same method. The same method of quantitation may be applied since they also contain phosphorus proportionally basically.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

DESCRIPTION OF THE PREFERRED EMBODIMENTS OF THE INVENTION

Figure 1:
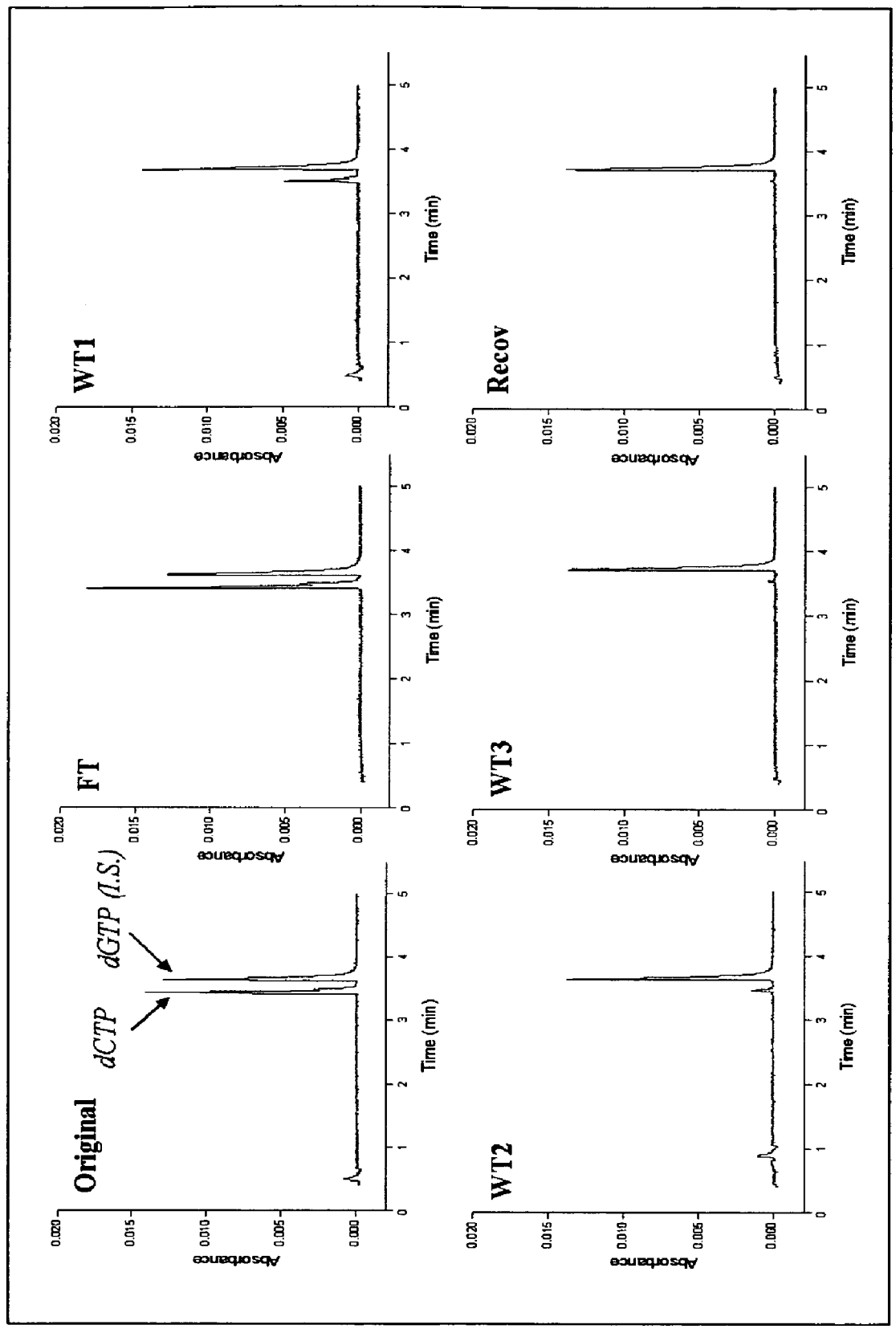
FIG. 1 shows removal of dCTP during the cleanup process as confirmed through CE.

Hereinafter, the present invention is illustrated more concretely in terms of preferred embodiments and examples.

Preferred Embodiment 1

Preparation and Purification of DNA Oligomers

A 20-mer oligomer (base sequence: OH-TAATACGACT-CACTATAGGG-OH) (SEQ ID No.: 1) was synthesized and purified through polyacrylamide gel electrophoresis (PAGE) in order to separate impurities. The PAGE-purified oligomer was quality assured using MALDI-TOF mass spectrometry, and freeze-dried. The freeze-dried oligomer was resuspended in deionized water, and further cleaned up through ultrafiltration with Centricon YM-3 columns (Millipore, Bedford, Mass., USA). Deionized water was prepared by passing tap water through a reverse osmosis system (Shinhanscience Tech, Daejon, Korea) and then a deionization system (Alpha-Q, Millipore, Bedford, Mass., USA). Concrete conditions are as shown below:

In detail, 120 vials of freeze-dried oligomer corresponding to 0.65 mg of oligomer in each vial were reconstituted and pooled together in 120 mL of deionized water. From the 120-mL original preparation, 96 mL was cleaned up through three independent 32-mL batch processes.

Then, each 32-mL oligomer solution batch was applied onto 16 Centricon columns and centrifuged for 2 hours at 7000 g. Centrifugation was performed using a Sorvall centrifuge (RC-28S, Du Pont, Wilmington, Del., USA), where the temperature of the centrifugation chamber was set at 10° C. For further cleanup, columns were washed with 2 mL of deionized water by centrifugation for 2 hours at 7000 g. The washing process was repeated once more, and each column retentate was recovered in approximately 1 mL of deionized water and pooled. The pool of recovered oligomer samples was then stored in Teflon bottles for later ICP-OES analysis.

EXPERIMENTAL EXAMPLE 1

Analysis of Removal Efficiency of Inorganic Phosphorus in Solutions During Quantitative Analysis of DNA Experiments for the evaluation of the possibility of complete removal of inorganic phosphorus dissolved in the solutions from the cleanup process through centrifugation using the above-described columns were performed. Removal of salts and inorganic phosphates by the purification process was estimated by measuring the electrical conductivities of all resulting solutions from the ultrafiltration process of sodium phosphate-spiked samples. Triplicate oligomer solutions (oligomer solutions I, II, and III) applied onto Centricon columns used in Preferred Embodiment 1 were mixed with equal volumes of 10 mM sodium phosphate having a pH of 7.0, and then subjected to ultrafiltration processes under the same conditions as those in Preferred Embodiment 1. The solutions from all ultrafiltration steps, as well as pure materials and the finally recovered solutions, were subjected to conductometry. A home-made conductometer with a miniature ring disk electrode-style probe was used, and conductivity was measured directly without further dilution. This instrument was calibrated to indicate $1.186 \times 10^{-5}$ $S \cdot cm^{-1}$ with 10.0 mM NaCl solution prior to use. It has been confirmed that measurement with the conductometer had an accuracy of within 2% (25?롤인요망) of measured values for NACl solutions in the concentration range of 0.01 to 100 mM.

Table 1 shows the results of experiments performed to determine the degree of removal of the above sodium phosphate.

TABLE 1

Conductivities of filtrate solutions from cleanup process

| Filtrates/ solutions | Oligomer solution ($S \cdot cm^{-1}$) | | | Deionized water ($S \cdot cm^{-1}$) |
| --- | --- | --- | --- | --- |
| | I | II | III | |
| Original | 4.88 | 4.88 | 4.88 | 4.76 |
| FT | 4.43 | 4.48 | 4.46 | 4.42 |
| WT1 | 1.14 | 1.09 | 0.99 | 0.99 |
| WT2 | 0.22 | 0.17 | 0.25 | 0.17 |
| WT3 | 0.06 | 0.06 | 0.04 | 0.04 |
| Recovered | 0.13 | 0.13 | 0.13 | 0.03 |
| Unspiked | 0.14 | 0.14 | 0.14 | 0.02 |

Note.
Conductivities (unit: $10^{-5}$ $S \cdot cm^{-1}$) of filtrate solutions of 50 mM sodium phosphate-spiked oligomer samples and deionized water.

Removal of phosphate ions during the cleanup process was demonstrated by the conductivity decay of the filtrate solutions from ongoing filtration steps. As seen in Table 1, the decrease in conductivity was in an exponential manner, as expected. The removal rate was consistent with the volume ratio of the flow through to the initial sample. In the case of the deionized water spiked with 50 mM phosphate, the conductivity of the solution from the second wash step (WT2) reached less than 1% of the original solution. Considering the highly effective PAGE cleanup procedure previously applied to the samples, it is concluded that sufficient removal of inorganic P, mainly phosphate ion, is ensured through the ultrafiltration cleanup. The conductivities of the recovered oligomer solutions were slightly smaller than that of the unspiked oilgomer solution (0.13 vs. 0.14 $S \cdot cm^{-1}$). If this difference is meaningful, it might be due to the loss of a minor portion of the oligomer itself during washing.

It was confirmed from the above results that inorganic phosphorus that might be included as an impurity in the step of purification of DNA oligomers was removed completely, and there was no loss of DNA oligomers during this process.

EXPERIMENTAL EXAMPLE 2

Analysis of Removal Efficiency of Small Organic Phosphorus Molecules in Solutions During Quantitative Analysis of DNA Experiments for the evaluation of the possibility of complete removal of small organic phosphorus molecules dissolved in the solutions from the cleanup process through centrifugation using the above-described Centricon columns were performed. Removal of small organic phosphorus molecules by the ultrafiltration cleanup was estimated by capillary electrophoresis (CE) analysis.

The degree of removal was evaluated by adding deoxycytidine triphosphate (dCTP) as a model molecule of organic phosphorus.

20 mM dCTP (D-4633, Sigma, St. Louis, Mo., USA) was spiked into the oligomer solution Centricon columns used in Preferred Embodiment 1 to make its final concentration 1.0 mM. The spiked solution was subjected to the cleanup process, and the resulting solutions were analyzed with a CE system (Model 270, ABLI, Foster City, Calif., USA) with a UV detector. Absorbance was measured at 280 nm. The CE instrument was operated in a reversed polarity mode with a buffer system of 20 mM Tris-HCl+1 mM cetyltrimethylammonium bromide (CTAB), pH 8.0. Uncoated fused silica capillaries having an inner diameter of 50 μm and an outer diameter of 379 μm were obtained from Polymicron Technologies (Phoenix, Ariz., USA) and used. The length of the separation capillary was 75 cm, with the length to the detection window being 60 cm. A high voltage of −25 kV was applied for electrophoresis, and the sample was injected for 10 seconds at −5 kV. Each solution from the cleanup process was mixed with an equal volume of 1 mM deoxyguanosine triphosphate (dGTP), which was then used as an internal standard for analysis.

Figure 2:
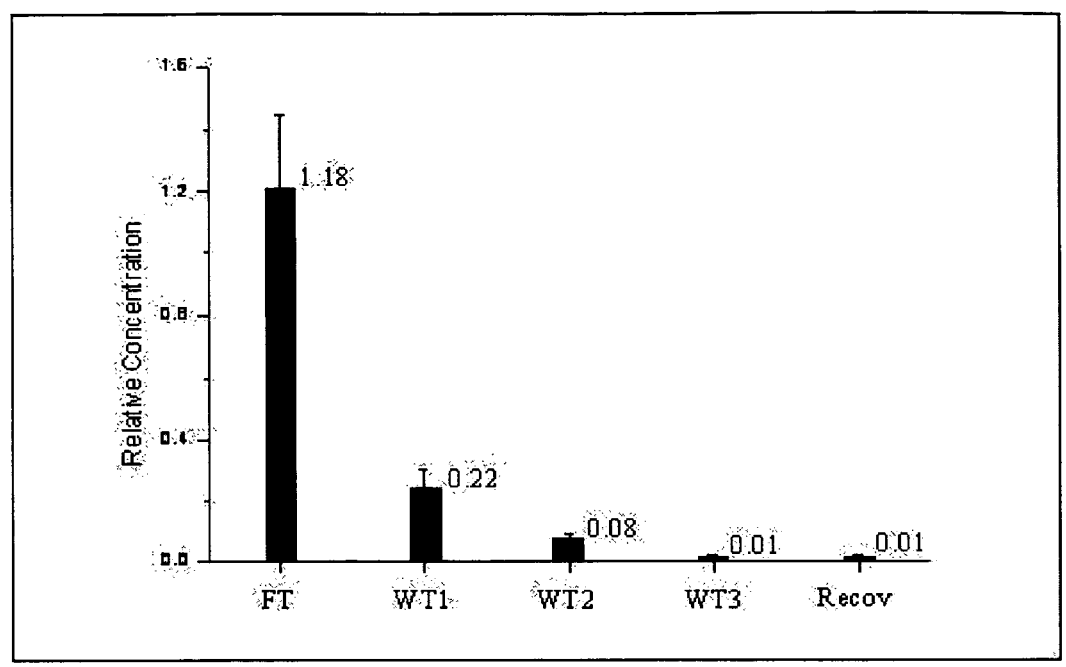
FIG. 2 shows decaying pattern of residual dCTPs in flow-through solutions from the cleanup process.

How effectively dCTP added was removed from the ultrafiltration cleanup was observed by capillary electrophoresis (CE). FIG. 2 shows the results of CE of the solutions derived from the cleanup process. Analytical performance was improved significantly by adding dGTP as an internal standard. Rapid migration and high sensitivity for the negatively charged analyte were achieved by employing the reversed polarity mode with the reversal of the electroosmotic flow using a CTAB-containing buffer system. In this mode of CE, negatively charged molecules migrate faster than neutral molecules.

FIG. 2 shows the rapid decrease of dCTP concentration during the progress of the cleanup process. The average concentration of dCTP in the recovered oligomer solutions was 11 μM, which was approximately 1% of the spiked concentration of 1 mM. In case of the samples after the PAGE cleanup, it was seen that it was possible to remove sufficiently small organic phosphorus molecules, that are the sources of contamination, with this capability of removal if the samples were contaminated while processing the samples.

EXPERIMENTAL EXAMPLE 3

Experiments to Confirm Loss of DNA Oligomers in Purified Solutions

The degree of loss of the target oligomer during the ultrafiltration cleanup process was exained by ICP-OES analysis of P in the resulting solutions from the process. The results are summarized in Table 2. In case of the first flow-through (FT), it was shown that it contained only 2% of P fraction of the original solution, but its concentration was reduced to 0.7% in the filtrate of the next wash step (WT1), and maintained on a level of 0.6% thereafter.

TABLE 2

P contents in the solutions from the cleanup process

|  | Original | FT | WT1 | WT2 | Recovered | Sum |
|---|---|---|---|---|---|---|
| Total P (mg) | 2.864 | 0.052 | 0.019 | 0.018 | 2.864 | 2.952 |
| P fraction | 1 | 0.018 | 0.007 | 0.006 | 1 | 1.031 |

Therefore, it was confirmed that the oligomer solutions cleaned by PAGE were nearly free of P-containing impurities, and the loss of the oligomer through the ultrafiltration cleanup process was insignificant. The P content in the recovered solutions was equivalent to that in the original solution within the measurement uncertainty.

EXPERIMENTAL EXAMPLE 4

Assessment of Molecular Purity Using MALDI-TOF MS

Figure 3:
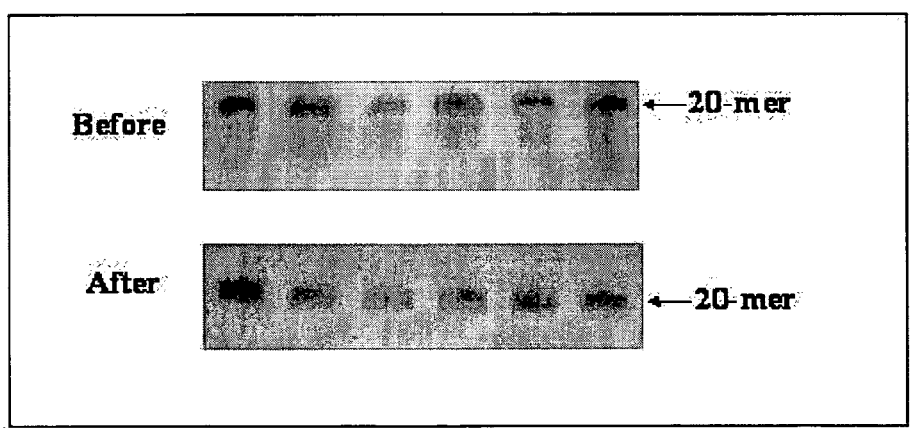
FIG. 3 shows how short oligomeric impurities are removed from the target 20-mer oligo by PAGE cleanup process.

Since impurities contributed by shorter oligomers leads to inaccuracy in the calculation of the mole concentration of oligomers, it is necessary to find out the concentration of short oligomer impurities accurately. Shorter fragments accompanied from the synthetic process of the oligomer are efficiently removed by PAGE purification. (Refer to FIG. 3.) However, it is still necessary to find out the concentrations of 18 mer, 19 mer, etc. that may remain in the cleaned-up 20-mer oligomer slightly.

Molecular purity of the target oligomer was estimated by MALDI-TOF MS analysis. The proportions of unwanted short forms of oligomer (18 and 19 mer) in the target sample were estimated semiquantitatively by the standard addition method. The 19-mer (sequence: AATACGACTCACTAT-AGGG) (SEQ ID NO.: 2) and 18-mer (sequence: ATAC-GACTCACTATAGGG) (SEQ ID NO.: 3) oligomers, that were necessary for the application of the standard addition method, were synthesized (Bioneer, Daejon, Korea) and spiked into the target oligomer to the weight portions of 2.5, 5.0, and 10.0%. Independently prepared 2-, 20-, and 200-µM solutions of standard-added samples were spotted on the 384 pad with precoated matrix (Spectro™, Sequenom, San Diego, Calif., USA) and analyzed with the Spectrocheck™ system (Bruker BiFlex III, Sequenom, San Diego, Calif., USA). The relative concentrations of 18-, 19-, and 20-mer impurities in the target oligomer were estimated based on the typical standard addition method.

Figure 4:
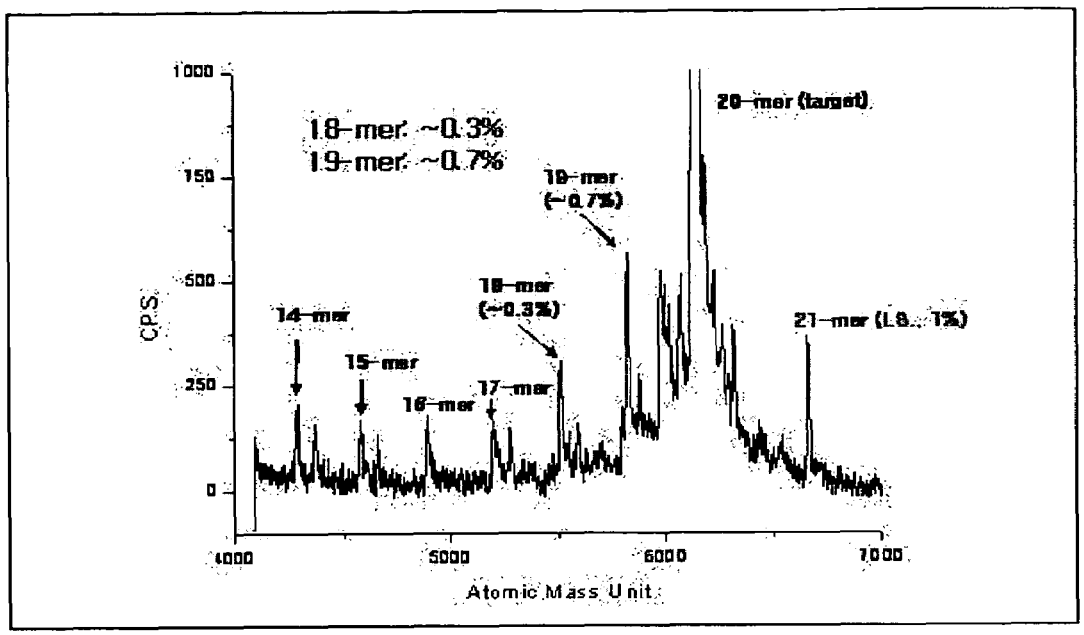
FIG. 4 shows mass spectrum of MALDI-TOF MS representing proportions of short oligomeric impurities.
Figure 5:
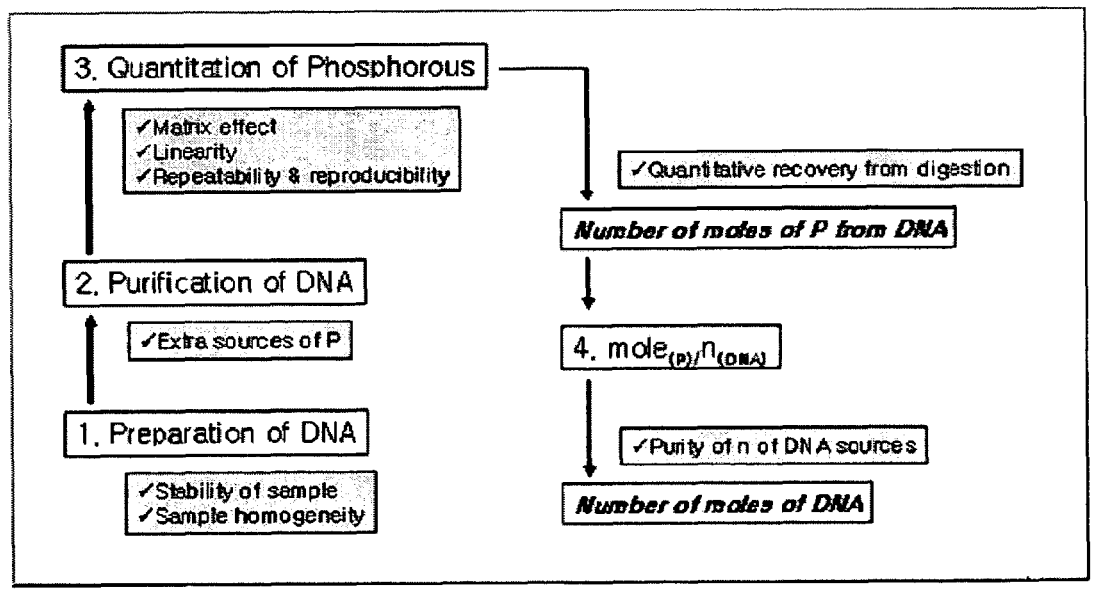
FIG. 5 shows a schematic of the overall processes for obtaining the number of moles of DNA by ICP-OES in the present invention.

FIG. 4 shows the original MALDI-TOF mass spectra. Although the peaks of 18 and 19 mer remained at the baseline level for the oligomer itself, the peaks of 18 and 19 mer are distinctively shown in case of standard-added samples. The standard addition method of 18- and 19-mer oligomer samples resulted in 1.0% ($R^2$=0.997) and 1.1% ($R^2$=0.998), respectively, of probable impurities, and the molecular purity of the 20-mer oligomer was determined to be 99±1%.

EXPERIMENTAL EXAMPLE 5

Validation Experiments of Inorganic P and Low-Molecular-Weight Organic P Using ICP-OES Reliability was evaluated for the validation of quantitative recovery of the acid digestion process by using standard solutions.

For this, the same sample preparation procedure was applied to three subsamples each of P standard solution and dTMP standard solution. Those subsamples were prepared gravimetrically to give approximately 200 mg/kg as P. A P standard solution was prepared from the primary P reference material (PRM) that is used for certification of certified reference materials (CRMs) of Korea Standard Science Research Institute. The P primary standard solution was prepared from high purity (99.999%) ammonium dihydrogen phosphate (Aldrich, St. Louis, Mo., USA). After purity assay and drying in an oven at 105° C. for 1 hour, the material was dissolved in 0.8% nitric acid to make approximately 1000-mg/kg P solution. The dTMP standard solution was prepared by gravimetrically dissolving an appropriate amount of dTMP into deionized water. The dTMP was obtained from Sigma (T-9758). The purity of dTMP assigned by the manufacturer, 96.5% after subtraction of the water content, was used with 3% standard uncertainty. Two procedure blanks were also prepared by sampling appropriate amounts of deionized water, to which the same sample preparation procedure was applied. Three calibration standard blends for P quantitation were prepared as follows. Appropriate amounts of the 1000-mg/kg P and Y standard solutions were combined and then diluted with deionized water, which is for closely matching the P/Y mass ratios and inorganic P concentrations, as well as nitric acid concentration, with those of the digested samples.

ICP-OES analysis of P, dTMP, and the oligomer samples was performed in an alternating measurement manner to minimize the adverse effect of instrumental drift. Samples consisted of 3 calibration standard blends and 10 digested sample blends. An Ultima ICP-OES (Jobin Yvon, Longjumeau, France) was used for analysis. The detailed ICP-OES conditions are listed in Table 3.

TABLE 3

| ICP-OES operating conditions ICP-OES | |
|---|---|
| Wavelength | 214.914 nm for P |
| Reference wavelength | 193.091 nm for Y |
| Plasma gas | 12.5 L/min |
| Auxiliary gas | 0.2 L/min |
| Nebulizer gas | 0.66 L/min |
| RF power | 1000 W |
| Nebulizer | Meihard concentric nebulizer |
| Spray chamber | Scott-type spray chamber |
| Sample uptake | 1.2 mL/min |

The amounts of P were determined based on the relative peak intensity ratio of P/Y to that of standard blends. The number of moles of P was calculated from the determined mass of the P divided by the atomic mass of P of 30.9736 g/mole. The number of moles of the target oligomer was calculated by dividing the number of moles of P by 19.

The results are shown in Table 4. For P standard solutions, the values expected from the gravimetric preparation of the solutions and the results of ICP-OES analysis were 195.67±0.49 and 196.17±0.58 mg/kg, respectively, which concurred with each other within the measurement uncertainty. For the dTMP standard solutions, the values expected from the gravimetric preparation of the solutions and the results of ICP-OES analysis were 202.12±6.29 and 203.97±0.62 mg/kg, respectively, which differed greatly. But these two values are deemed to concur with each other considering the overwhelmingly large uncertainty of the expected value.

Therefore, the quantitative analysis by the ICP-OES method was determined to be reliable.

TABLE 4

Validation result for the microwave-aided digestion process

| P concentration (mg/kg) with standard uncertainties | P standard solution | DTMP standard solution |
|---|---|---|
| Prepared[a] | 195.67 ± 0.49 | 202.12 ± 6.29 |
| Measured | 196.17 ± 0.58 | 203.97 ± 0.62 |

[a]P concentrations according to gravimetric preparation of samples.

Preferred Embodiment 2

Quantitation of Oligomer P Using ICP-OES

A 20-mer target oligomer (sequence: OH-TAATAC-GACTCACTATAGGG-OH) (SEQ ID NO.: 1) was synthesized and then purified through polyacrylamide gel electrophoresis (PAGE). The PAGE-purified oligomer was quality assured using MALDI-TOF MS and freeze-dried.

The freeze-dried oligomer was resuspended in deionized water and further cleaned up through ultrafiltration with Centricon YM-3 columns (Millipore, Bedford, Mass., USA). Deionized water ware prepared by passing tap water through a reverse osmosis system (ShinhanScience Tech, Daejon, Korea) and then a deionization system (Alpha-Q, Millipore, Bedford, Mass., USA). 120 vials of freeze-dried oligomer corresponding to 0.65 mg of oligomer in each vial were reconstituted and pooled together in 120 mL of deionized water. From the 120-mL original preparation, 96 mL was cleaned up through three independent 32-mL batch processes.

Then 32 mL of oligomer solution was applied onto 16 Centricon columns and centrifuged for 2 hours at 7000 g. Centrifugation was performed using a Sorvall centrifuge (RC-28S, Du Pont, Wilmington, Del., USA) where the temperature of the centrifugation chamber was set at 10° C. For further cleanup, columns were washed with 2 mL of deionized water by centrifugation for 2 hours at 7000 g. The washing process was repeated once more, after which each column retentate was recovered in approximately 1 mL of deionized water.

For quantitation of P in the target oligomer solution recovered, four subsamples of the target oligomer solution were taken and weighed accurately to have a weight of 200 mg/kg as P. The solutions were transferred to 100-mL Teflon high-pressure acid-digestion vessels and spiked with an appropriate amount of yttrium (Y) internal standard solution. The final concentrations of P and Y were to be 10 and 5 mg/kg, respectively. Followed by the addition of 1 mL each of subboiled $HNO_3$ into digestion vessels, oligomer samples were subjected to digestion using an MLS 1200 mega Microwave Labstation (Milano, Italy). The microwave digestion conditions were in the order of for 2 minutes at 250 W—2 minutes at 0 W—5 minutes at 250 W—5 minutes at 400 W—10 minutes at 600 W. All of acid-digested samples were nearly completely transferred to polyethylene bottles and diluted to 30 g with deionized water.

Acid-digested samples were subjected to ICP-OES analysis under the same conditions as those in Table 3 of Experimental Example 5.

The total P content in the finally purified oligomer sample was determined to be 192.08 mg/kg with a standard uncertainty of 0.66 mg/kg, as shown in Table 5. That is equivalent to 6.2014±0.0213 mole/kg. Although the standard uncertainty was 0.34% of the measured value, the expanded uncertainty was calculated to be 0.6% due to the limited number of samples.

TABLE 5

Concentration of P in the acid-digested oligomer (mg/kg)
Sample blends

| I | II | III | IV |
|---|---|---|---|
| 192.69 | 191.47 | 191.75 | 192.42 |

Average = 192.08
Standard uncertainty = 0.66 (0.34%)

The concentraiton of the oligomer was calculated to be 0.32639±0.00275 mmole/kg, assuming the numer of phosphodiester bonds of 19. The number of bonds was 19 since —OH radical, instead of phosphate, was attached at the 5' terminus. However, there would be a problem if the number 19 was applied simply in case of the impurities of 18 and 19 mer. In this case, since the purity of 20 mer was known to be 99±1% by MALDI-TOF MS, the concentration of 20 mer was calculated to be 0.32338±0.00275 mmole/kg when the uncertainty was increased to 1.6%.

COMPARATIVE EXAMPLE 1

Measurement of UV OD and Calculation of the Concentration from the OD Value

UV OD of the target oligomer used in Preferred Embodiment 2 was measured with a dual-beam UV spectrometer (UV-2501PC, Shimadzu, Kyoto, Japan). A quartz UV cell (QS 1.000, Perkin-Elmer, Wellesley, Mass., USA) with a nominal cell path length of 1.000 cm was used. The UV absorption measurement system was calibrated with 0.08 g/kg $K_2Cr_2O_7$ (SRM 913c, National Institute of Standards and Technology [NIST], Gaithersburg, Md., USA) in 0.001 N perchloric acid according to the information on its extinction coefficient given in the certificate of NIST SRM 935a. The analytical target solution was 100-fold diluted with deionized water in a gravimetric manner for measurement of UV absorption.

The concentration of the oligomer obtained through a conventional calculation method based on UV $OD_{260}$ and that determined by ICP-OES were compared with each other. The instrument for UV measurement was calibrated with high-purity $K_2Cr_2O_7$SRM from NIST (99.984%, SRM 136c). The measured value was 1.810±0.0003, whereas the theoretically calculated absorbance was 1.813, indicating high accuracy of the UV OD measurement. The $OD_{260}$ of the 100-fold dilution of the purified target oligomer solution was measured as 0.5535±0.0003. Applying this $OD_{260}$ value to the equation of the nearest neighbor estimates, the concentrations were calculated and compared with the ICP-OES result. The results are summarized in Table 6.

TABLE 6

Comparison of the concentrations of the oligomer calculated from UV OD$_{260}$ data with the results of the ICP-OES procedure

| ICP-OES | UV OD$_{260}$ | |
|---|---|---|
| (mmole/kg) | Conventional[1] (mmole/L) | Cavaluzzi[2] (mmole/L) |
| 0.3264 ± 0.0028 | 0.2913 ± 0.0002 | 0.2978 ± 0.0002 |

[1] Calculated in the "nearest neighbor estimates" method by using the UV absorbance of dNMP known generally. (Nucleic Acids Res., 32, 2004, e13, 19.)
[2] Calculated by using the UV absorbance of dNMP measured newly and precisely. (Handbook of Biochemistry and Molecular Biology, 3rd Ed., CRC Press, Cleveland, OH, USA, Vol. 1, pp. 589-595.)

All concentrations calculated from the UV OD data were shown to be smaller than the value determined by the ICP-OES procedure. Assuming that the concentrations determined using the ICP-OES procedure was inherently accurate from their measurement principle, the degree of underestimation by the UV OD$_{260}$ measurement was between 8 and 10%, which concurred with a trend that the extinction coefficients of oligomers were overestimated compared to actual values according to other research groups' observations. Cavaluzzi and Borer have reported an average 14% overestimation of extinction coefficients for their 18-mer test oligomer. (Cavaluzzi, M. J. et al., Nucleic Acids Res., 2004, 32, e13, 19.; Murphy, J. H. et al., Anal. Biochem., 240, 1996, 273-282.)

Therefore, it is seen that ICP-OES of the present invention is more accurate since obtaining the underestimated concentration for the target oligomer is unavoidable because the calculated concentration is reciprocally related to the extinction coefficient.

INDUSTRIAL APPLICABILITY

In the present invention, the number of moles of an oligomer was determined from the moles of P atoms determined by ICP-OES. By applying the metrologically well-established analytical procedure, the concentration of P was determined with an accuracy of within 0.6% while maintaining the traceability to a Standard International (SI) unit, the mole. 100% recovery of P from the acid digestion procedure was proven by using the dTMP model compound.

It was proven that potential sources of P other than the analytical target oligomer, i.e., other types of inorganic P or organic compounds, were well removed through the cleanup process. It was confirmed that both sodium phosphate and dCTP were reduced down to 1% of the spiked concentrations through three cleanup processes. The recovery of the oligomer itself was nearly 100%. The molecular purity of the target oligomer was assessed to be about 99±1% from a standard addition experiment using MALDI-TOF MS.

If oligomers are purified according to the method in the present invention, effects of removal of other types of inorganic P or organic compounds, other than oligomers, may be obtained.

Also, there is an effect of the quantitation of desired DNA by employing the method according to the present invention, and it is expected to have very large spin-off effects on the bio field in that the absolute quantitation certified reference materials of synthetic DNA oligomers are to be developed and distributed for the first time in the world.

While certain present preferred embodiments and examples of the present invention have been shown and described, it is to be distinctly understood that the invention is not limited thereto but may be otherwise variously embodied and practiced within the scope of the following claims.

What is claimed is:

1. A method for quantitation of nucleic acid comprising steps of:
   1) cleaning up a sample comprising a nucleic acid by filtering to remove phosphorous-containing compounds other than said nucleic acid;
   2) digesting said nucleic acid by adding a acid to the filtered sample from step 1);
   3) quantifying phosphorous content in the sample by using inductively coupled plasma-optical emission spectrometry (ICP-OES); and
   4) calculating quantity of said nucleic acid from the quantity of phosphorous based on the stoichiometry between phosphorous and nucleotide units in said nucleic acid.

2. The method for quantitation of nucleic acid of claim 1 wherein effective cleaning up is confirmed by removal of control phosphorous containing compounds compounds introduced to the sample prior to filtering.

3. The method for quantitation of nucleic acid of claim 1 wherein effective cleaning up is confirmed by conductometry, capillary electrophoresis or MALDI-TOF analysis.

4. The method of quantitation of nucleic acid of claim 1 wherein said nucleic acid is a synthetic oligonucleotide DNA, genomic DNA, plasmid DNA or RNA.

5. The method of quantitation of nucleic acid of claim 1 further comprising, adding yttrium to the filtered sample as an internal standard prior to digesting said nucleic acid.

* * * * *